United States Patent [19]
Eckhouse et al.

[11] Patent Number: 5,836,999
[45] Date of Patent: *Nov. 17, 1998

[54] METHOD AND APPARATUS FOR TREATING PSORIASIS USING PULSED ELECTROMAGNETIC RADIATION

[75] Inventors: Shimon Eckhouse; Michael Kreindel, both of Haifa, Israel

[73] Assignee: ESC Medical Systems Ltd., Yokneam, Israel

[ * ] Notice: The term of this patent shall not extend beyond the expiration date of Pat. No. 5,405,368.

[21] Appl. No.: 535,705

[22] Filed: Sep. 28, 1995

[51] Int. Cl.$^6$ .................................................... A61N 5/06
[52] U.S. Cl. .............................. 607/88; 607/90; 607/94; 606/3
[58] Field of Search ................... 607/88–89, 90, 607/91, 94; 606/11–17, 2–6

[56] References Cited

U.S. PATENT DOCUMENTS

| | | |
|---|---|---|
| 4,022,534 | 5/1977 | Kishner . |
| 4,298,005 | 11/1981 | Mutzhas . |
| 4,757,431 | 7/1988 | Cross et al. . |
| 4,784,135 | 11/1988 | Blum et al. . |
| 4,829,262 | 5/1989 | Furumoto . |
| 4,840,798 | 6/1989 | Skaliots .................................. 424/488 |
| 4,926,861 | 5/1990 | Fengo et al. ............................. 607/88 |
| 4,930,504 | 6/1990 | Diamantopoulos et al. . |
| 4,950,880 | 8/1990 | Hayner . |
| 5,161,526 | 11/1992 | Hellwing et al. . |
| 5,207,671 | 5/1993 | Franken et al. . |
| 5,217,455 | 6/1993 | Tan . |
| 5,259,380 | 11/1993 | Mendes et al. . |
| 5,320,618 | 6/1994 | Gustafsson . |
| 5,344,418 | 9/1994 | Ghaffari . |
| 5,344,434 | 9/1994 | Talmore . |
| 5,405,368 | 4/1995 | Eckhouse .................................. 607/88 |
| 5,454,807 | 10/1995 | Lennox et al. ............................ 606/17 |

FOREIGN PATENT DOCUMENTS

3906860-A1  9/1989  Germany .

OTHER PUBLICATIONS

Diffusion of Light in Turbid Material, A. Ishimaru, Applied Optics 1989, vol. 28, No. 12, pp. 2210–2215.
Role of Skin Optics in Diagnostic and Therapeutic Uses of Lasers, S. L. Jacques, Springer–Verlag, 1991, pp. 1–21.

*Primary Examiner*—John P. Lacyk
*Attorney, Agent, or Firm*—Foley & Lardner

[57] ABSTRACT

A method and apparatus for treating psoriasis includes a source of incoherent electromagnetic energy. The energy is directed to a region of tissue to be treated. The pulse duration and the number of pulses may be selected to control treatment parameters such as the heating of healthy tissue and the penetration depth of the energy to optimize the treatment. Also, the radiation may be filtered to control the radiation spectrum and penetration depth. The filtering may include attenuating an UV portion of the radiation spectrum and portions of the spectrum below a desired treatment bandwidth. A light guide for large or small spot sizes may be used to direct the light to the skin. A cooling gel is applied to the skin to be treated in another embodiment. The gel may be cooled either before or after it is applied to the skin.

12 Claims, 1 Drawing Sheet

METHOD AND APPARATUS FOR TREATING PSORIASIS USING PULSED ELECTROMAGNETIC RADIATION

FIELD OF THE INVENTION

The present invention relates generally to a method and apparatus for treating psoriasis. More particularly, the invention relates to treating psoriasis by irradiating psoriatic plaques with visible and near infrared electromagnetic radiation.

BACKGROUND OF THE INVENTION

Psoriasis is a relatively common skin disease that appears in a few percent of the population. Prior art treatments of psoriatic plaques fall generally into two categories: the use of a topical drug (i.e., a drug that is applied to the skin externally) and the application of light to the psoriatic plaques. However, many of these prior art techniques have a common fundamental drawback: they offer relief to the patient for only a limited time.

The topical drug treatment includes treatment by coal and wood tar dithranol and corticosteroids. These treatments produce acceptable results that last for no more than a few weeks. Detergent shampoos, salicylic acid ointments are also used, but they are also limited in their efficiency and the length of time of relief for the patient.

Treatments utilizing light generally use a portion of the electromagnetic spectrum. For example, ultraviolet light in the UVA and UVB ranges is used extensively. This method of treatment offers a very limited relief to the patient and is used on a very frequent basis (typically once a week). Moreover, it provides limited clinical improvement and there is a risk of skin cancer due to the use of UV radiation. A psoriasis treatment using $CO_2$ laser light has also been tried with limited success.

A more recent prior art treatment of psoriasis uses a pulsed dye laser operating at a wavelength of 585 nm, with a pulse duration of 0.4 msec and fluences in the range of 6 to 10 $J/cm^2$. While this treatment was generally effective, one significant drawback is the small spot size (of the order of 5 mm) of a pulsed dye laser. The small spot size makes the treatment very inefficient since psoriasis typically appears on large areas of the skin. Thus, the treatment becomes a time consuming procedure for the patient. The pulsed dye laser has other shortcomings when used to treat psoriasis related to the fixed and relatively short pulse of this laser, and to the limited degree of tunability of this laser.

Accordingly, a method and apparatus for treating psoriasis that provides effective relief for a relatively long period of time is desirable. Additionally, the method and apparatus will preferably be efficient for treating relatively large areas of skin. Preferably, the treatment will utilize pulsed electromagnetic radiation in the visible and/or near infrared portions of the spectrum and overcome the drawbacks of the prior art treatments.

SUMMARY OF THE PRESENT INVENTION

According to a first aspect of the invention a method for treating psoriasis includes generating one or more pulses of incoherent electromagnetic energy and directing the energy to a region of tissue to be treated. The pulses may have energy fluences in the range of 5 $J/cm^2$ to 200 $J/cm^2$. In an alternative embodiment the pulse duration and the number of pulses are selected to control a treatment parameter and optimize the treatment. The parameters that are controlled include the heating of healthy tissue and the penetration depth of the energy. In another alternative the radiation is filtered, thus controlling the radiation spectrum and penetration depth. The filtering may include attenuating an UV portion of the radiation spectrum. In one embodiment a large spot size is created to treat large area psoriasis plaque. A cooling gel is applied to the skin to be treated in another embodiment. The gel may be cooled either before or after it is applied to the skin.

An apparatus for the treatment of psoriatic plaque includes a housing that has a window, in accordance with a second aspect of the invention. A light source that produces incoherent radiation in the visible and near infrared range of wavelength is placed in the housing. A reflector reflects and directs the light through the window to the plaque that must be treated. A filter removes unwanted portions of the spectrum, such as light in the UV range. The filter system may include a fixed filter that attenuates the UV light and a variable filter that attenuates light below a selectable wavelength. Alternatively, the variable filter may pass a selected bandwidth. In another embodiment a light guide is placed between the window and the skin to be treated, and directs the light to the skin. The light guide may be a flexible light guide for a small spot size or a quartz light guide for large spot sizes. Additionally, the light guide may filter a portion of the spectrum. A power supply that includes a pulse generator is provided to power the light source in one embodiment. In another embodiment a microprocessor controls the power supply and the pulse duration and pulse delay. The microprocessor may also include a display for displaying suggested treatment parameters.

A third aspect of the invention is a method of protecting a region of epidermis during a treatment of psoriasis. The protection is effected by applying a gel to the region of epidermis to cool the epidermis. The gel may be cooled before or after it is applied to the epidermis.

Other principal features and advantages of the invention will become apparent to those skilled in the art upon review of the following drawings, the detailed description and the appended claims.

Figure 1:
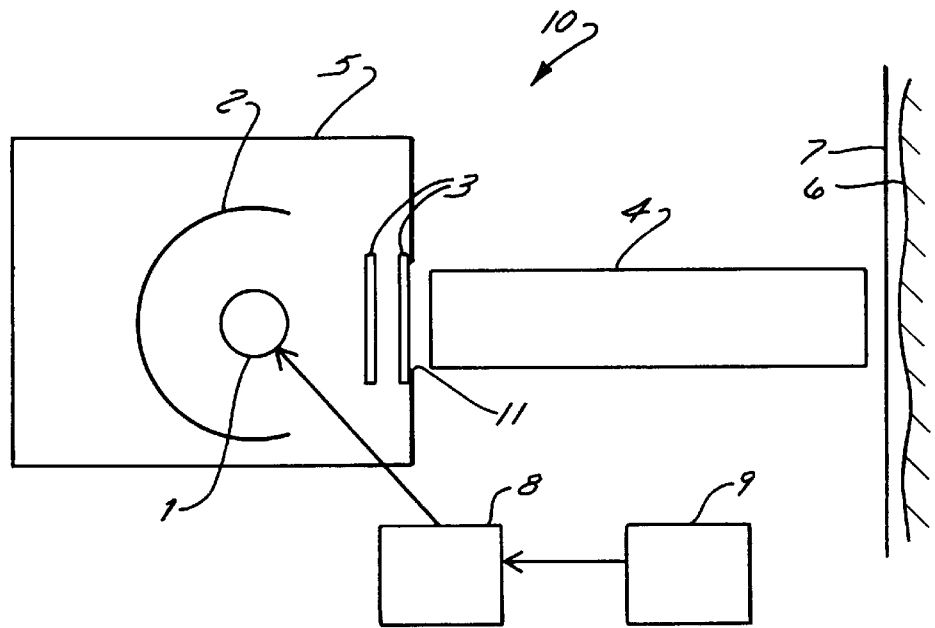
FIG. 1 is a schematic illustration of one preferred embodiment of the present invention.

Before explaining at least one embodiment of the invention in detail it is to be understood that the invention is not limited in its application to the details of construction and the arrangement of the components set forth in the following description or illustrated in the drawings. The invention is capable of other embodiments or being practiced or carried out in various ways. Also, it is to be understood that the phraseology and terminology employed herein is for the purpose of description and should not be regarded as limiting.

DETAILED DESCRIPTION OF THE PREFERRED EMBODIMENTS

The invention relates to a new method and apparatus for treating psoriasis. Generally, the invention uses pulsed light, preferably incoherent, in the visible range, that causes the clearance of psoriatic plaque. In accordance with one preferred embodiment, the apparatus includes a light source that provides electromagnetic radiation that penetrates into the skin, and reaches depths of the order of 1 mm or more. Preferably, the fluence of the light will be sufficient to enable coagulation of the vessels feeding the lesion and the abnormal cells. The light is applied to the skin in pulses to help limit any damage to healthy tissue that surrounds the unhealthy tissue, that might otherwise be caused by heat conductivity. Also, the spot size of the light will preferably be large enough, in the centimeter range, e.g., to enable efficient treatment of large areas of skin.

An apparatus in accordance with one preferred embodiment of the invention includes a high energy, pulsed, incoherent light source, such as a flashlamp. A suitable flashlamp (typically in a linear configuration) will generate pulsed light in the visible and near infrared range of wavelength. The apparatus includes a fixed filter system which cuts off the radiation spectrum, thus reducing the amount of electromagnetic radiation of damaging wavelengths that reaches the skin. Also, a variable filter system that has lower cut off filters that allow radiation above a given wavelength to be transmitted to the skin is provided in one embodiment. Alternatively, the lower cut off filters allow a selected bandwidth of wavelength to be transmitted to the skin. The selection of the variable filter (and thus the wavelength of the transmitted light) will allow the optimal treatment to be provided.

The light is directed to the skin through an opening in a housing that contains the flashlamp and the filter system in one embodiment. In another embodiment a light guide connected to the housing and in contact with, or in the vicinity of, the skin is used to direct the light to the treatment area. Preferably, the system will produce fluences on the skin in the range of up to a few to hundreds of joules per square centimeters in either embodiment.

A coupling gel that can be used in some cases to enhance light coupling to the skin and enable better cooling of the epidermis during treatment.

An apparatus made in accordance with the present invention is useful for treatment of psoriasis. High energy pulsed light can be an effective way of selective photothermolysis of blood vessels and other parts of unhealthy tissue without damage of normal skin. Moreover, an apparatus made in accordance with the present invention is safe and there is little risk of accidental injury to the operator and patient.

Referring now to FIG. 1, a treatment device 10 for treating a region of skin 6 made in accordance with the present invention is schematically shown and includes a flashlamp 1 and a reflector 2 disposed in a housing 5. In the preferred embodiment flashlamp 1 has a linear shape, although other shapes could be used.

Flashlamp 1 may be operated in pulse mode and produce light radiation able to penetrate into a tissue at the millimeter depth or deeper. The pulse rate and delay rate may be selected to provide high radiation density on the treated surface and avoid the overheating of surrounding health tissue due to heat conductivity process. A fluence in the range of from a few joules to more than tens of joules on the surface of skin 6 over an area of several square centimeters, and preferably in the range of from 5 J/cm$^2$ to hundreds of J/cm$^2$ (200 J/cm$^2$, e.g.) is provided by flashlamp 1. The light source will preferably provide a spot size variable from at least some centimeters to some millimeters.

Reflector 2 forms the light beam and reflects it to a light guide 4. In one embodiment reflector 2 may be a metallic reflector. Typically, polished aluminum, which is an easily machinable reflector and has a very high reflectivity in the visible range of the spectrum, can be used. Other bare or coated metals can also be used. Reflector 2 preferably has a shape and cross section to focus light produced by flashlamp 1 at a desired location, such as at the proximal end of light guide 4, or on the surface of skin 6 which is to be treated. One such reflector is described in U.S. Pat. No. 5,405,368, which is hereby incorporated by reference.

A filter system 3 is disposed within housing 5, adjacent an opening or window 11. Filter system 3 is thus located in the path of light directed from the flashlamp 1 to the light guide 4 and/or skin 6, and will affect the spectrum of light provided by device 10. Filter system 3 includes one or more fixed filters that attenuate electromagnetic radiation having wavelengths (such as light in the UV range) that will damage the skin and/or overheat shallow layers of skin. Also, in one embodiment, filter system 3 includes one or more variable filters that have lower cut off filters and allow radiation above a given wavelength to be transmitted to the skin. In an alternative embodiment the variable filters transmit a selected bandwidth of wavelength to the skin, thus reducing the need for the fixed filters.

The depth the treatment light penetrates into the tissue or skin 6 is dependent upon the wavelength of the incident light (as will be discussed in greater detail below). Thus, the penetration depth may be controlled by the selection of the filters. Accordingly, the selection of the variable filter (and thus the wavelength of the transmitted light) may be done to optimize the treatment.

Additionally, in an alternative embodiment spectral control is achieved by controlling the parameters of the pulse provided to flashlamp 1. For example, a spectrum with longer wavelengths may be obtained by decreasing the arc current in the flashlamp.

A power source 8 provides power to flashlamp 1 to produce the pulsed light output. Power source 8 preferably provides single or multiple pulses with delay between pulses which varies from several milliseconds to hundreds of milliseconds. The total fluence to the treated area is the product of the number of pulses and the fluence per pulse and preferably may reach a value of hundreds of joules per square centimeter. The pulse duration can be varied in the range of hundreds of microseconds to tens of milliseconds in the preferred embodiment, and the fluence per pulse is variable in the range of a few joules to hundreds of joules per square centimeters. Power source 8 may include a pulse forming network, such as that shown in U.S. Pat. No. 5,405,368, or other circuitry to produce the desired pulses.

Pulse parameters are controlled by a microprocessor based controller 9 in the preferred embodiment. Microprocessor based controller 9 provides the timing functions and prompts the trigger signals that cause power supply 8 to deliver the pulses of power to flashlamp 1. In one embodiment power supply 8 and controller 9 are disposed within housing 5.

In an alternative embodiment microprocessor based controller 9 includes a user interface, such as a display screen and keyboard, buttons, mouse, or other input device, and may be a personal computer. Controller 9 may have information stored therein that aids in the selection of treatment parameters. The physician inputs patient information, such as the depth needed to be treated, and the microprocessor provides suggested treatment parameters, such as wavelength, filter selection, pulse width, and pulse delay. The physician can alter these suggested parameters, but need not refer back to operating guidelines for suggested parameters. This alternative may be used with light sources other than a flashlamp, such as UV or a pulsed laser.

Light guide 4 directs the light to the treatment area on skin 6. If the area to be treated is difficult to access objects or small plaques are to be treated, light guide 4 may be a flexible light guide with the spot size of several millimeters. Alternatively, if large areas are to be treated light guide 4 may be a broad quartz light guide with a spot size of several centimeters, or the use of a light guide may be omitted altogether.

Light guide 4 may be used for spectral control in one alternative embodiment. Spectral control can be achieved by making the light guide from a material that had an absorbing dye dissolved therein. Thus, light transmitted by the light guide will have a spectrum as determined by the absorbing dye.

The treatment is accomplished by coagulation of hemoglobin and overheating of tissue with abnormal pigmentation. However, to avoid overheating of normal epidermis and decrease pain, a transparent gel 7 may be applied on treated skin surface 6.

The cooling time t of an epidermis that has typical dimension d and diffusivity a can be written as:

$$t = d^2/a$$

The epidermis has typical cross dimensions of less than 0.1 mm. The diffusivity is approximately $a = 3 \times 10^{-7} m^2 sec^{-1}$. When a gel is applied the typical cooling time of the epidermis will be on the order of 30 msec. Application allows the epidermis to cool during a pulse and to avoid adverse effects if the light pulse duration is approximately the same as the cooling time of the epidermis. In order to increase the cooling effect the gel may be previously cooled down. Alternatively, the gel may be cooled after it is applied to the skin.

Figure 2:
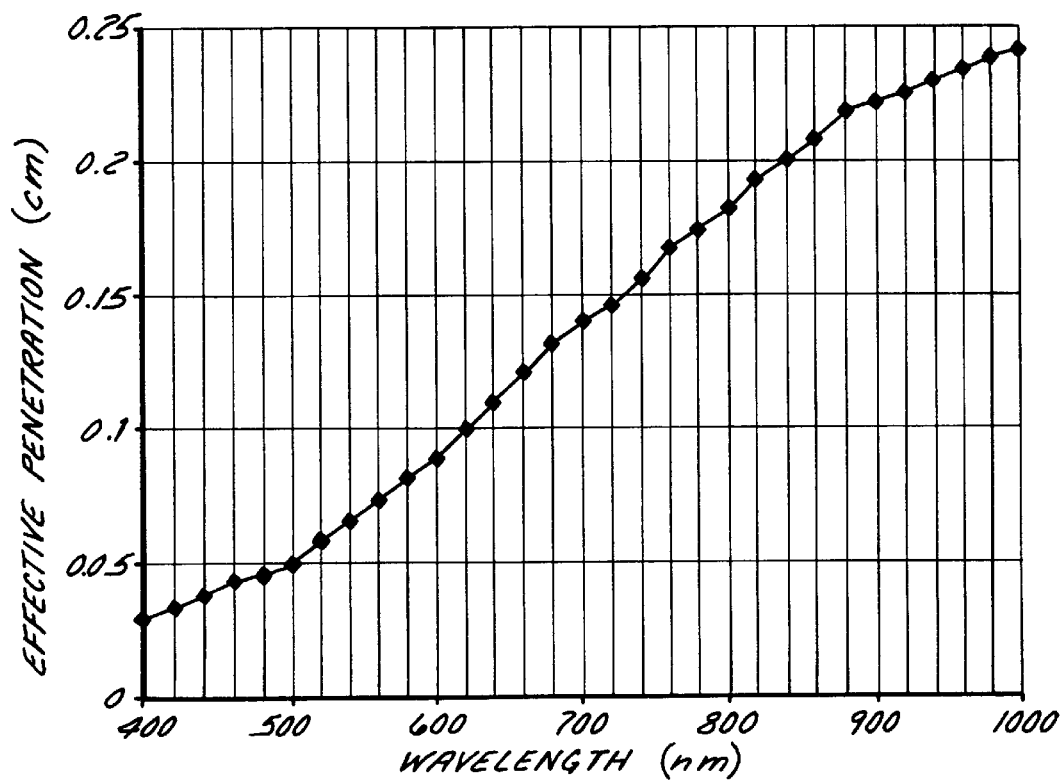
FIG. 2 is a graph of the effective penetration depth of light into the bloodless skin (dermis) as a function of wavelength in the range of 400 nm to 1000 nm.

As stated above, depth of penetration can be controlled by selection of appropriate wavelength range. The effective depth of penetration into the skin can be estimated by using the effective attenuation coefficient of the dermis that takes into account scattering and absorption of light. As described in S. L. Jacques, *Role of Skin Optics in Diagnostic and Therapeutic Uses of Lasers*, Springer-Verlag, 1991, pp. 1–21, effective attenuation coefficient of the skin can be written as:

$$\mu_{eff} = [3\mu_a(\mu_a + \mu_s(1-g))]^{1/2}$$

where $\mu_a$ is an absorption coefficient of dermis, $\mu_s$ is a scattering coefficient of dermis, g is the anisotropy factor which is defined as the average cosine of the scattering angle for one scattering event. The effective penetration depth which can be estimated from $$d = 1/\mu_{eff}$$

and is shown in the FIG. 2 as a function of wavelength in the range of 400 nm to 1000 nm. As shown, radiation with longer wavelengths penetrates deeper into the skin than radiation of shorter wavelengths.

The effective penetration depth d is defined as the depth at which the fluence impinging of the skin reaches 1/e of the value on the surface of the skin. As shown in FIG. 2, penetration goes up by a factor of almost two when the wavelength is increased from 500 nm to 600 nm. Penetration depths of 2 mm can be achieved at a wavelength of 800 nm. Thus, in the preferred embodiment the spectrum of the light that reaches skin 6 has a wavelength selectable over the range of 400 nm to 1000 nm, and particularly from the range of 500 nm to 600 nm and as high as 800 nm. As stated above the spectrum may be controlled using filters, light guides, or pulse widths. Thus, proper filtering and the use of a gel allows selectivity of treatment to be achieved by selection of a desired spectrum of radiation and by cooling shallower skin layers.

Thus, it should be apparent that there has been provided in accordance with the present invention a method and apparatus for treating psoriasis that fully satisfy the objectives and advantages set forth above. Although the invention has been described in conjunction with specific embodiments thereof, it is evident that many alternatives, modifications and variations will be apparent to those skilled in the art. Accordingly, it is intended to embrace all such alternatives, modification and variations that fall within the spirit and broad scope of the appended claims.

The embodiments of the invention in which an exclusive property or privilege is claimed are defined as follows:

1. A method of treating psoriasis comprising the steps of generating at least one pulse of incoherent electromagnetic energy and directing the pulse of electromagnetic energy to a psoriatic plague to be treated.

2. The method of claim 1 further including the steps of providing a plurality of pulses, selecting a pulse duration and selecting a number of pulses to control a treatment parameter.

3. The method of claim 2 further including wherein the pulse duration and number of pulses are selected to prevent overheating of healthy tissue adjacent to the psoriatic plaque.

4. The method of claim 2 further including wherein the pulse duration and number of pulses are selected to control a penetration depth.

5. The method of claim 1 including the step of filtering the at least one pulse to control a radiation spectrum to control a penetration depth.

6. The method of claim 5 wherein the step of filtering includes the step of attentuating an UV portion of the radiation spectrum.

7. The method of claim 1 including the step of providing a spot size of several centimeters to treat a large area psoriasis plaque.

8. The method of claim 1 wherein the at least one pulse includes a plurality of pulses.

9. The method of claim 1 wherein the at least one pulse has an energy fluence in the range of 5 J/cm$^2$ to 200 J/cm$^2$.

10. The method of claim 1 including the step of applying a transparent gel to the psoriatic plaque to cool the plaque.

11. The method of claim 10 including the step of cooling the gel prior to the step of applying the gel.

12. The method of claim 10 including the step of cooling the gel after the step of applying the gel.

* * * * *